United States Patent
Foelling

(10) Patent No.: US 10,338,369 B2
(45) Date of Patent: Jul. 2, 2019

(54) METHOD AND DEVICE FOR SETTING A SUITABLE EVALUATION PARAMETER FOR A FLUORESCENCE MICROSCOPE

(75) Inventor: Jonas Foelling, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 632 days.

(21) Appl. No.: 13/577,951

(22) PCT Filed: Jan. 3, 2011

(86) PCT No.: PCT/EP2011/050011
§ 371 (c)(1),
(2), (4) Date: Aug. 9, 2012

(87) PCT Pub. No.: WO2011/098304
PCT Pub. Date: Aug. 18, 2011

(65) Prior Publication Data
US 2012/0305803 A1    Dec. 6, 2012

(30) Foreign Application Priority Data
Feb. 12, 2010    (DE) .................. 10 2010 007 730

(51) Int. Cl.
*G01N 21/64*    (2006.01)
*G02B 21/16*    (2006.01)
(Continued)

(52) U.S. Cl.
CPC ......... *G02B 21/16* (2013.01); *G01N 21/6458* (2013.01); *G02B 21/367* (2013.01); *G02B 27/58* (2013.01)

(58) Field of Classification Search
CPC ...... G02B 21/16; G02B 21/367; G02B 27/58; G01N 21/6458
See application file for complete search history.

(56) References Cited

U.S. PATENT DOCUMENTS 4,741,043 A    4/1988    Bacus
5,885,840 A *  3/1999    Kamentsky et al. ........... 436/63
(Continued)

FOREIGN PATENT DOCUMENTS

DE        3689856 T2      9/1994
DE     102005018092 A1   11/2005
(Continued)

OTHER PUBLICATIONS

Egner et al. Fluorescence nanoscopy in whole cells by asynchronous localization of photoswitching emitters, Biophysical Journal vol. 93, No. 9 (Nov. 2007), pp. 3285-3290.*
(Continued)

*Primary Examiner* — David P Porta
*Assistant Examiner* — Shun Lee
(74) *Attorney, Agent, or Firm* — Leydig, Voit & Mayer, Ltd.

(57) ABSTRACT

A method for setting an evaluation parameter for a fluorescence microscope includes exciting dye particles in a sample to fluoresce and detecting fluorescent light from the particles. A graphical representation of a distribution of the fluorescent light is determined and a signal is generated for use in displaying the graphical representation on a display unit. Each subregion of the graphical representation is associated with a comparison value that is representative of a light quantity in the subregion. A predefined threshold is used as an evaluation parameter and compared to the comparison values. The subregions having a comparison value that is greater than the threshold value are marked on the display unit with predefined markings. The threshold value is changed and the comparison values are compared to the changed threshold value. The marked regions are defined as events and a complete image of the sample is obtained based on the events.

12 Claims, 2 Drawing Sheets

(51) Int. Cl.
   *G02B 21/36* (2006.01)
   *G02B 27/58* (2006.01)

(56) References Cited

U.S. PATENT DOCUMENTS

| | | |
|---|---|---|
| 6,371,908 B1 | 4/2002 | Furusawa et al. |
| 7,117,098 B1 | 10/2006 | Dunlay et al. |
| 7,580,185 B2 | 8/2009 | Haisch et al. |
| 2005/0232488 A1* | 10/2005 | Lee ............... G06K 9/00127 382/190 |
| 2005/0239117 A1 | 10/2005 | Tanaami et al. |
| 2007/0081078 A1* | 4/2007 | Cummings ........... G02B 21/06 348/79 |
| 2008/0182336 A1 | 7/2008 | Zhuang et al. |
| 2009/0134342 A1* | 5/2009 | Hell et al. .................. 250/459.1 |
| 2009/0242798 A1 | 10/2009 | Bewersdorf et al. |
| 2011/0043619 A1 | 2/2011 | Wolleschensky |

FOREIGN PATENT DOCUMENTS

| | | |
|---|---|---|
| DE | 102008021641 A1 | 11/2009 |
| DE | 102008024568 A1 | 12/2009 |
| DE | 102008027403 A1 | 12/2009 |
| EP | 2110697 A1 | 10/2009 |
| JP | 2006226916 A | 8/2006 |
| JP | 2009517665 A | 4/2009 |
| WO | WO 2006012769 A1 | 2/2006 |
| WO | WO 2009132811 A1 | 11/2009 |

OTHER PUBLICATIONS

European Patent Office, International Search Report in International Patent Application No. PCT/EP2011/050011 (dated Apr. 18, 2011).
Geisler, et al., Resolution of $\lambda/10$ in fluorescence microscopy using fast single molecule photo-switching, Appl. Phys. A 88, p. 223-226, Jun. 1, 2007.

* cited by examiner

METHOD AND DEVICE FOR SETTING A SUITABLE EVALUATION PARAMETER FOR A FLUORESCENCE MICROSCOPE

CROSS REFERENCE TO RELATED APPLICATIONS

This application is a U.S. National Phase application under 35 U.S.C. § 371 of International Application No. PCT/EP2011/050011, filed on Jan. 3, 2011, and claims benefit to German Patent Application No. DE 10 2010 007 730.5, filed on Feb. 12, 2010. The International Application was published in German on Aug. 18, 2011 as WO 2011/098304 A1 under PCT Article 21 (2).

FIELD

The present invention relates to a method and device for setting a suitable evaluation parameter for a fluorescence microscope.

BACKGROUND

In fluorescence microscopy, fluorescent dye particles in a sample are excited to fluoresce. The dye particles in the sample are bound to molecules of the sample, so that detection of the fluorescent light allows conclusions to be drawn about structures and processes in the sample. The fluorescent dye particles are also referred to as marker substances or markers. The fluorescent dye particles are either naturally present in the sample, or artificially incorporated into the sample and coupled to the molecules of the sample.

Some fluorescence microscopes are capable of imaging structures in a sample which are smaller than the diffraction resolution limit of conventional light microscopes. Furthermore, these fluorescence microscopes are able to image processes taking place in an area smaller than the diffraction resolution limit of conventional light microscopes. These fluorescence microscopes are based on sequential, stochastic localization of dye particles. The dye particles have two distinguishable states. In a first active state, the dye particles can be excited to fluoresce, while in a second inactive state, the dye particles cannot be excited to fluoresce. Moreover, the dye particles can be transferred from the active to the inactive state, or from the inactive to the active state.

In order to overcome the resolution limit imposed by diffraction, a large portion of the dye particles are transferred to the inactive state, or only a small fraction are transferred to the active state, so that, as a result, only a relatively small fraction of the dye particles are in the active state. Switching from the active state to the inactive state, or from the inactive state to the active state, can be accomplished in different ways.

International Publication WO 2006/12769 A2 describes a switching process from an active state to an inactive state, and then from an inactive state to an active state. In particular, dye particles are used which can be transferred from the inactive state to the active state by irradiation with light of a defined activation wavelength. A portion of the dye particles in the active state can be returned to the inactive state by bleaching, which further reduces the subset of active dye particles. Subsequently, the remaining active dye particles of the subset are excited to fluoresce by the excitation light.

In the publication Appl. Phys. A, 88, 223-226, 2007, a method is described which uses dye particles capable of being reversibly transferred from the inactive state to the active state by irradiation with light of a defined activation wavelength, and of being reversibly returned from the active state to the inactive state by irradiation with light of a defined deactivation wavelength. The active dye particles are excited to fluoresce by the excitation light.

German Publication DE 10 2008 024 568 A1 describes the use of dye particles which have transient dark states, such as triplet states. A large portion of these dye particles are transferred to the dark state, and automatically return to the active state with a defined probability after a residence time which is dependent on the type of molecule.

The methods described in the above-mentioned documents are known under the names of PALM, FPALM, (F)STORM, PALMIRA, dSTORM and GSDIM. All these methods have in common that only a subset of dye particles is transferred to the active state and excited to fluoresce while in the active state. The subset of active dye particles must be so small that the average distance between neighboring dye particles in the active state is greater than the conventional resolution limit of the imaging optical system. The fluorescent light from the subset of active dye particles is imaged onto a spatially resolving photodetector, such as a CCD camera, in particular an EM-CCD camera. The use of a spatially resolving photodetector makes it possible to then display a graphical representation of the fluorescent light distribution which is representative of a distribution of the fluorescent dye particles in the sample. In particular, the graphical representation of the light distribution exhibits light spots whose size is determined by the unsharpness of the imaging optical system and which are representative of the dye particles in the sample. For each of the light spots, a comparison value representative of a light quantity causing the light sport is determined using known algorithms. If the comparison value is greater than a predefined threshold value, then the light spot is classified as an event. Subsequently, additional images are captured, which show further light spots, at least a portion of which are then classified as events. Then, an image of the searched structures or processes in the sample is generated based on all events. The threshold value may also be referred to as evaluation parameter. The comparison value may be, for example, a light quantity, a light intensity, a light energy, or a luminance within the subregion of the graphical representation of the light distribution that causes the light spot. The selection of a suitable evaluation parameter is decisive for the quality of the final image.

SUMMARY

In an embodiment, the present invention provides a method for setting a suitable evaluation parameter for a fluorescence microscope includes exciting fluorescent dye particles in a sample to fluoresce and detecting fluorescent light from the dye particles. A graphical representation of a distribution of the fluorescent light is determined and a representative signal is generated. The signal is used to display the graphical representation of light distribution on a display unit. Each of a plurality of subregions of the graphical representation of the light distribution is associated with a respective comparison value that is representative of a light quantity in the respective subregion. A predefined threshold is used as an evaluation parameter and compared to the comparison values. The subregions having a comparison value that is greater than the threshold value are marked on the display unit with predefined markings. The threshold value is changed in accordance with a user input and the comparison values are compared to the threshold values. The marked regions are defined as events and a complete image of the sample is obtained based on the events.

BRIEF DESCRIPTION OF THE DRAWINGS

Exemplary embodiments of the present invention are described in more detail below with reference to the schematic drawings, in which.

Elements having the same design or function are identified by the same reference numerals throughout the figures.

DETAILED DESCRIPTION

Figure 1:
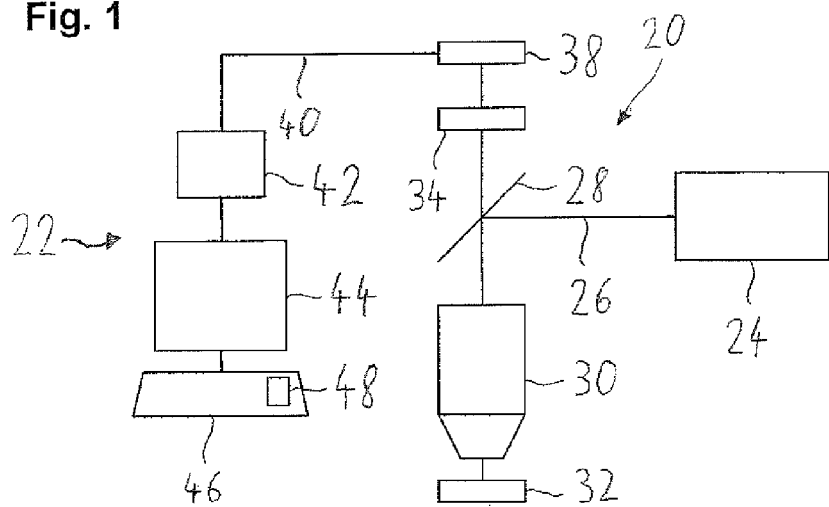
FIG. 1 shows a fluorescence microscope.

The present invention relates to a method and device for setting a suitable evaluation parameter for a fluorescence microscope. In this context, fluorescent dye particles in a sample are excited to fluoresce, and the fluorescent light originating from the dye particles is detected. A graphical representation of the fluorescent light distribution is determined, which is representative of a distribution of the light quantity on a detector of the fluorescence microscope. Subregions of the graphical representation of the light distribution are each associated with a respective comparison value which is representative of the light quantity in the corresponding subregion. A predefined threshold value is used as an evaluation parameter. The comparison values are compared to the predefined threshold value. Subregions whose comparison value is greater than the threshold value are classified as events.

In an embodiment, the present invention provides a method and a device for setting a suitable evaluation parameter for a fluorescence microscope which enable the evaluation parameter to be selected in an advantageous manner so as to generate a high-quality image of the desired structures or processes in the sample.

In an embodiment, a signal representative of the graphical representation of the light distribution is generated based on the detected fluorescent light. Based on this signal, a display unit is controlled to display the graphical representation of the light distribution. The subregions whose comparison value is greater than the threshold value are marked on the display unit with predefined markings. A predefined threshold value is used as an evaluation parameter. Depending on a user input, the threshold value is changed. After the user input, the comparison values are compared to the changed threshold value. The marked subregions are defined as events. A complete image of the sample is obtained based on the events.

The marking of the subregions whose comparison value is greater than the threshold value allows a user to suitably adjust at least one evaluation parameter, in particular the threshold value, prior to classification of the events. This contributes, in a surprisingly simple manner, to enable optimal selection of the threshold value. In particular, light spots caused by noise can be prevented from being defined as events. Thus, only those light spots appearing in the subregions are defined as events which are really caused by fluorescent dye particles.

In an embodiment, those subregions are marked on the display unit whose comparison value is greater than the adjusted threshold value. Thus, the user is given direct feedback as to whether the changed threshold value is more suited than the original predefined threshold value. The displaying of the graphical representation of the light distribution and the marking of the subregions can take place during the operation of fluorescence microscope and, in particular, during the detection of the fluorescent light, and thus during the capture of additional partial images. Alternatively, or in addition, it is possible to store the captured partial images of the corresponding light distributions, and to place the markings and adjust the threshold values during later processing, especially also when the fluorescence microscope is not in use.

The complete image of the sample is generated by determining for each event one point representative of a position of the dye particle that causes the event, such as, for example, a centroid or center point of the corresponding light spot of the graphical representation of the light distribution. Then, the partial images are all combined, during which process the complete image of the sample, especially of the desired structures and/or processes in the sample, is obtained based on said points.

The diffraction resolution limit is advantageously overcome by using dye particles which have an active state and an inactive state. During the capture of the partial images, only the subset of dye particles is transferred to the active state, or a large portion of the dye particles is transferred to the inactive state, and the subset of active dye particles is excited to fluoresce. The subset of active dye particles is selected such that an average distance between the active dye particles in the sample is smaller than the conventional resolution limit of the fluorescence microscope.

FIG. 1 shows a confocal fluorescence microscope 20 and a computing terminal 22. Fluorescence microscope 20 includes a light source 24 which produces a light beam 26. Light beam 26 strikes a beam splitter 28, which reflects light beam 26 to an objective 30, which focuses light beam 26 onto a sample 32. Sample 32 includes fluorescent dye particles. Fluorescent light originating from sample 32 passes through objective 30 and beam splitter 28 and reaches a color filter. The fluorescent light that passes through color filter 34 is directed onto a detector 38. A signal line 40 connects detector 38 to an evaluation unit 42 of computing terminal 22. Evaluation unit 42 is coupled to a display unit 44 and a keyboard 46. Keyboard 46 has an adjustment wheel 48. Computing terminal 22 and fluorescence microscope 20 are shown greatly simplified. Alternatively, the two systems may include additional or alternative components known in the art of fluorescence microscopy.

Light source 24 includes a first laser unit and a second laser unit. The first laser unit produces light of a first wavelength, which is hereinafter referred to as "excitation light". The second laser unit produces light of a second wavelength, which is hereinafter referred to as "activation light". Alternatively, it is possible to provide only one laser unit, whose light is split into a first sub-beam and a second sub-beam; the wavelength of one of the two sub-beams subsequently being converted. The wavelengths of the converted and unconverted sub-beams are selected such that one of the two sub-beams is the excitation beam and the other is the activation beam. Alternatively, it is possible to provide a broadband light source, for example, a white-light laser or a mercury vapor light source, whose light is split into subbeams; the desired wavelengths then being isolated by filtering the light produced. Light beam 26 is composed of the collinearly combined excitation light and activation light.

The dye particles in sample 32 are particles which have an active state and an inactive state. In other words: the dye particles are either in the active state or the inactive state.

Detector 38 is an area detector and includes a CCD camera. Alternatively, the area detector may take the form of an EM-CCD camera.

The excitation beam and the activation beam are collinearly combined in light source 24. The activation beam activates a subset of the dye particles in sample 32. Alternatively, the dye particles may first be activated, or be present in the active state, and then be deactivated by a deactivation beam. Alternatively, or in addition, dye particles in the active state may be transferred to the inactive state, for example, by bleaching. Moreover, it is possible to use dye particles which automatically change from the excited state to the inactive state, and then automatically change to the non-excited active state, which eliminates the need for an activation beam. The excitation beam excites the active dye particles to fluoresce. The fluorescent light has other wavelengths than the excitation light, the activation light and, if applicable, the deactivation light.

Beam splitter 28 allows the fluorescent light, which is shifted in wavelength from the excitation and activation beams, to pass therethrough to color filter 34. Color filter 34 then filters different wavelength ranges out of the fluorescent light. The fluorescent light of the remaining wavelengths is detected by detector 38. Thus, a plurality of light spots are produced on detector 38, the positions of which are representative of positions of the dye particles in sample 32 which cause the light spots.

The signals of detector 38 are transmitted from detector 38 to evaluation unit 42 through signal line 40. Evaluation unit 42 generates a signal that is representative of a graphical representation of the light distribution on detector 38, and thus of the distribution of the dye particles. Display unit 44 is controlled by this signal to display the graphical representation of the light distribution.

Figure 2:
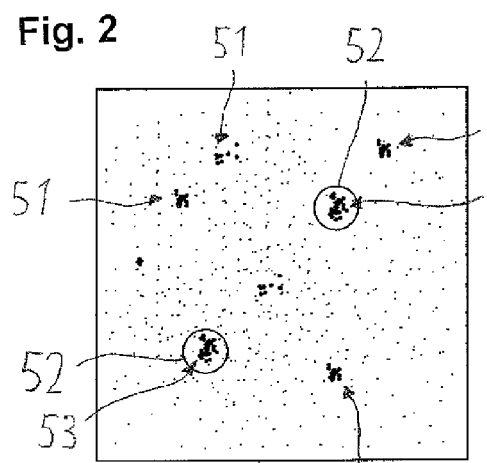
FIG. 2 shows a first partial image.

FIG. 2 shows a first partial image 50, which has been captured by detector 38 and is displayed on display unit 44. First partial image 50 shows a graphical representation of a light distribution having first subregions 51, which contain light spots which are due to real events, but have not been identified as such; and further having second subregions 53, which contain light spots which are due to real events and have been identified as such, and which further contain a multitude of unmarked small dots and light spots which have not been marked and are not due to real events, but to the noise of detector 38. In this exemplary embodiment, different light quantities are represented by dots of different sizes and dots with different spacings therebetween. Alternatively, or in addition, the different light quantities may also be represented by dots of different brightness. Evaluation unit 42 analyzes the signal of detector 38 using known algorithms, and identifies larger light spots, in particular subregions within the displayed graphical representation of the light distribution within which a light quantity is greater than a predefined threshold value. The light quantity may also be referred to as comparison value. Thus, evaluation unit 42 associates each subregion or light spot of the graphical representation of the light distribution with a respective comparison value. As an alternative to the light quantity within the subregions, the light intensity, the luminance, the luminous energy or the light energy within the respective subregions may also be used as a comparison value.

All subregions whose comparison value is greater than the predefined threshold value are classified as second subregions 53 and marked with predefined markings 52. Predefined markings 52 each include a circle. Alternatively, the markings may also have other geometric shapes or be represented by different colors. All subregions whose comparison value is smaller than the predefined threshold value are classified as first subregions 51, and thus as noise, and are not marked with predefined markings 52. However, the non-marked light spots may perfectly well be due to real events and correspond to positions of dye particles in sample 32. In particular, the light spots in first subregions 51 are caused by real events.

Figure 3:
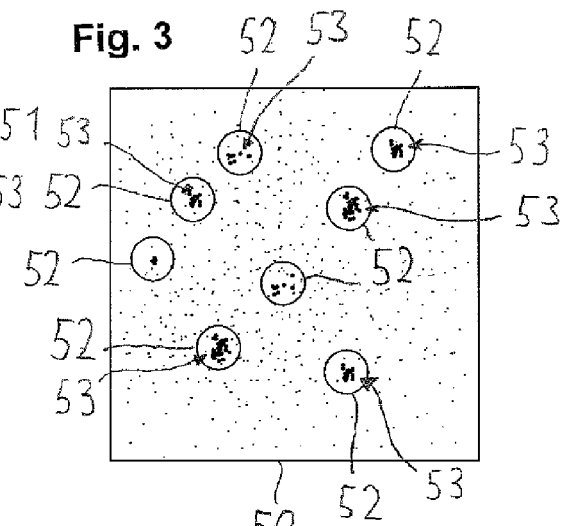
FIG. 3 shows a second partial image.

FIG. 3 shows first partial image 50 after a reduction in the threshold value used in the evaluation algorithm for comparison to the comparison value. Compared to first partial image 50 shown in FIG. 2, now all larger light spots are marked. In particular, second subregions 53 which are not caused by noise and which represent the positions of dye particles are now marked, as well as two subregions which are caused by noise and do not represent positions of dye particles in sample 32. Consequently, the threshold value was reduced too much.

Figure 4:
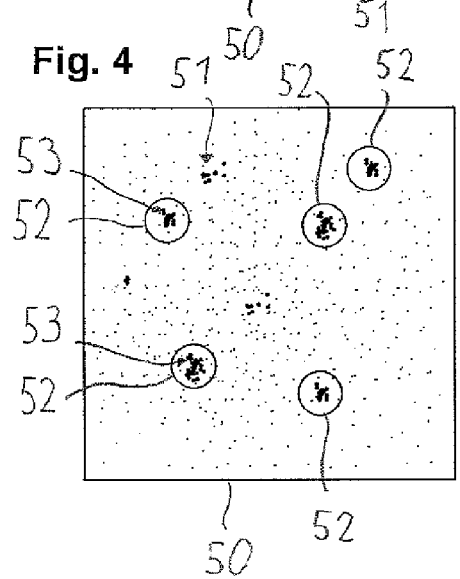
FIG. 4 shows a third partial image.

FIG. 4 shows first partial image 50 with an optimally selected threshold value. Here, only and all of those second subregions are marked whose light quantity is not caused by noise, but by the fluorescence of dye particles in sample 32, and thus by real events.

Figure 5:
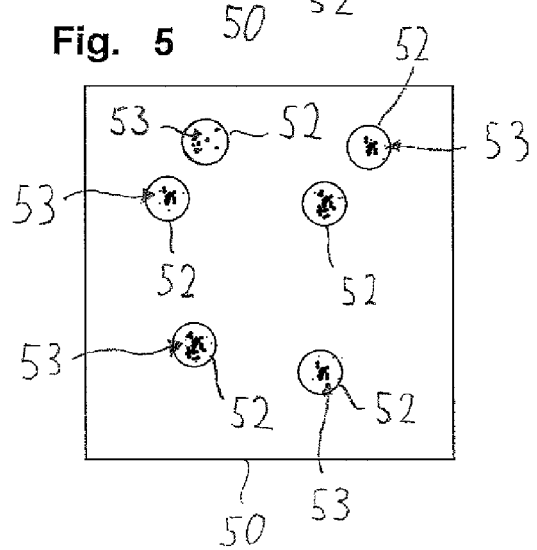
FIG. 5 shows a fourth partial image.

FIG. 5 shows partial image 50 after all signals outside the marked subregions 53 have been removed. The remaining light spots of the graphical representation of the light distribution within second subregions 53 are subsequently classified as events 55. FIG. 5 is for illustration purposes only. In real processing of the partial images, the noise does not have to be removed, but is simply excluded from the evaluation.

Figure 6:
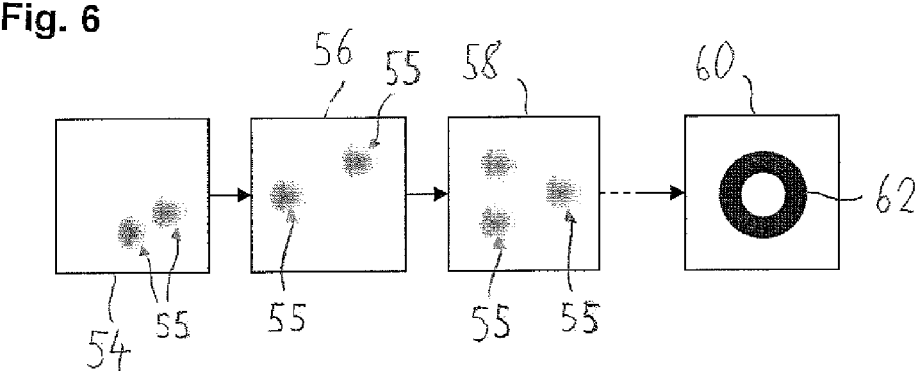
FIG. 6 shows several partial images and a complete image.

FIG. 6 shows a second partial image 54, a third partial image 56 and a fourth partial image 58, which only show events 55. In addition to these, many more partial images are captured. Sample 32 is illuminated over an extended period of time. Subsequently, partial images 50, 54, 56, 58 captured during this period of time are combined to form a complete image 60. Complete image 60 shows a structure 62 within sample 32. Details of the shown structure within sample 32 are smaller than the diffraction resolution limit of fluorescence microscope 20.

Figure 7:
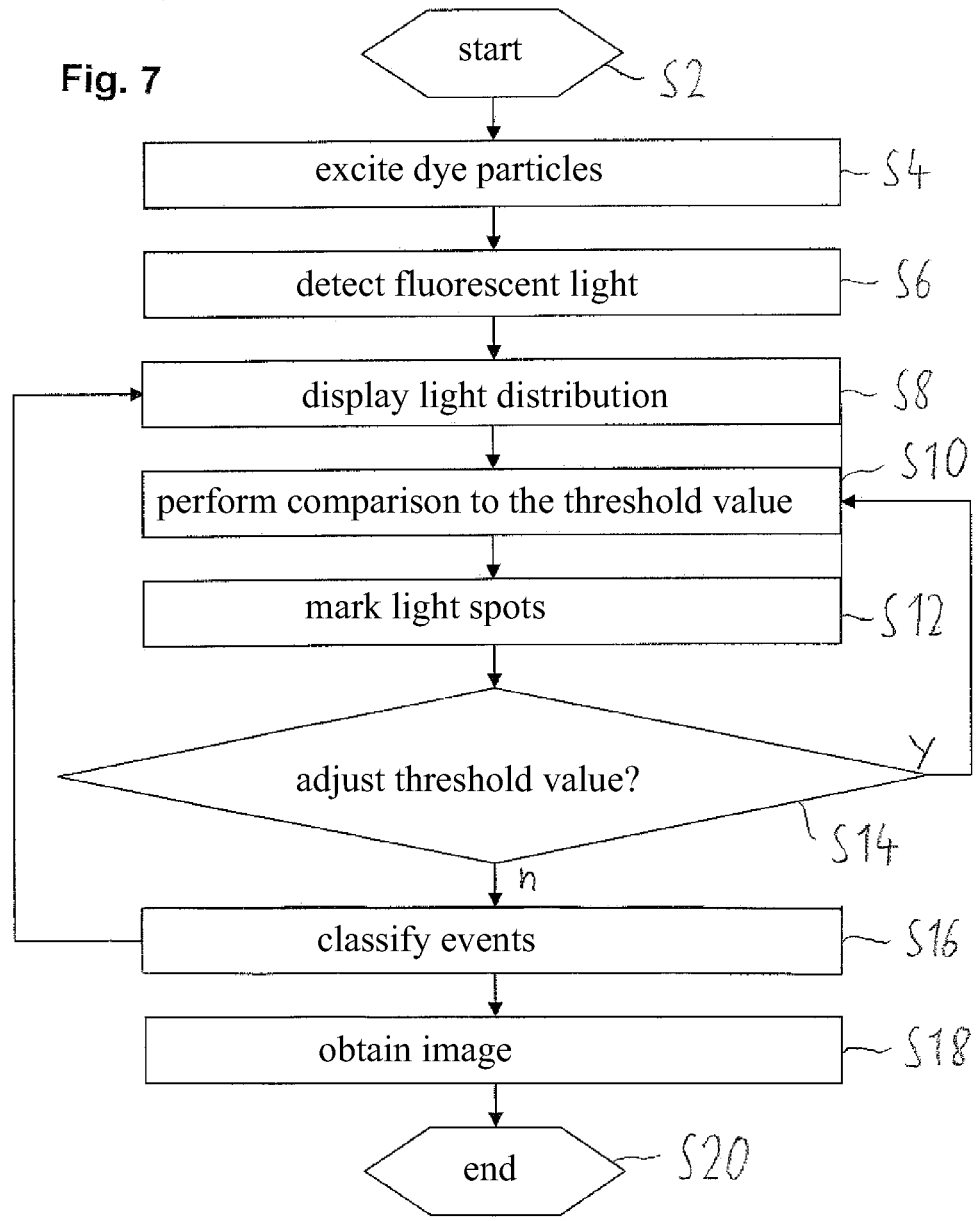
FIG. 7 shows a flow chart of a program for obtaining a complete image of a sample.

FIG. 7 shows a flow chart of a program for operating computing terminal 22 and fluorescence microscope 20, in particular for setting a suitable evaluation parameter, especially the threshold value, for fluorescence microscope 20. The program is started in a step S2, for example, when fluorescence microscope 20 is put into operation.

In a step S4, the dye particles are excited to fluoresce by the excitation light. In particular, the active dye particles of sample 32 are excited to fluoresce. In order to enable fluorescence microscope 20 to image structures smaller than the diffraction resolution limit of fluorescence microscope 20, only a subset of the dye particles is transferred to the active state. This may be done, for example, by transferring nearly all dye particles to the inactive state, so that only the subset of dye particles in the active state will remain. This subset can then be excited by the excitation beam. The subset is so small that the average distance of the dye particles of the subset is greater than the diffraction resolution limit of fluorescence microscope 20.

In a step S6, the fluorescent light is detected.

In a step S8, the graphical representation of the light distribution is displayed on display unit 44.

In a step S10, the comparison values are determined for the light spots of individual subregions of the displayed graphical representation of the light distribution and compared to the predefined threshold value. For example, a reference value may be used as the predefined threshold value. The threshold value may also be referred to as evaluation parameter.

In a step S12, the light spots and subregions within which the light quantity is greater than the predefined threshold value are marked with predefined markings 52.

In a step S14, a user of computing terminal 22 is given the possibility of adjusting the threshold value by a corresponding input. If the user changes the threshold value, processing returns to step S10. If the threshold value is not changed by the user, processing continues in step S16.

In step 16, the light spots within the marked subregions are defined as events 55, and the corresponding partial image of events 55 is stored. After that, step S8 is executed for a new partial image until sufficient images have been captured to obtain the complete image of the sample. During this process, steps S4 and S6 are permanently executed in the background.

In step S18, a point representative of the position of the dye particle that causes a particular event 55 is determined for each of the events 55. It is possible to determine, for example, the center points or centroids of the light spots classified as events 55. The complete image of sample 32 is then obtained based on these points by combining the points of all partial images to form the complete image 60.

In a step S20, the program may be terminated. Preferably, however, the program is continuously executed during the operation of fluorescence microscope 20. Alternatively, it is possible to execute steps S2 and S4 during the operation of fluorescence microscope 20 and to store the raw data acquired. The evaluation of the data according to steps S8 through S20 may be performed at any desired time, especially when fluorescence microscope 20 is not in use and/or in a different place than where fluorescence microscope 20 is located.

The present invention is not limited to the exemplary embodiments described herein. For example, the subset of active dye particles may be produced by transferring only the subset of dye particles from the inactive state to the active state. Alternatively, it is possible to use dye particles which automatically return to the active state with a defined probability. In this case, initially all dye particles in the sample are transferred to the inactive state, and image acquisition is performed after at least one period of time, or after several periods of time, has or have elapsed after the deactivation of the dye particles. Furthermore, as an alternative to the light quantity, the graphical representation of the light distribution may also be determined by displaying the light energy, the luminous energy, the luminance or the light intensity in a spatially resolved manner, in which case the comparison value is the light quantity, the light energy, the luminous energy, the luminance, or the light intensity, respectively.

LIST OF REFERENCE NUMERALS 20 confocal fluorescence microscope
22 computing terminal
24 light source
26 light beam
28 beam splitter
30 objective
32 sample
34 color filter
38 detector
40 signal line
42 evaluation unit
44 display unit
46 keyboard
48 adjustment wheel
50 first partial image
51 non-marked subregion
52 marking
53 marked subregion
54 second partial image
55 event
56 third partial image
58 fourth partial image
60 complete image
62 structure
S2-S20 steps two through twenty
y adjust the threshold value
n do not adjust the threshold value
START start of program
ENDE end of program

What is claimed is:

1. A method for setting and using a suitable evaluation parameter for stochastic localization microscopy imaging with a fluorescence microscope, the evaluation parameter being useable to prepare for generation of a complete localization microscopy image, the method comprising:

prior to generating a complete localization microscopy image:
exciting fluorescent dye particles in a sample to fluoresce;
detecting fluorescent light originating from the fluorescent dye particles;
determining, for a first one of a plurality of partial images taken during the detecting of the fluorescent light, a graphical representation of a distribution of the fluorescent light that is representative of a distribution of a light quantity on a detector of the fluorescence microscope;
generating a signal representative of the graphical representation of the light distribution;
displaying the graphical representation of the light distribution on a display unit based on the generated signal;
associating each of a plurality of subregions of the graphical representation of the light distribution with a respective comparison value that is representative of a light quantity in the respective subregion;
using a predefined threshold value as an evaluation parameter during taking of the partial images which are later used to form the complete localization microscopy image;
comparing the comparison values to the threshold value;
marking subregions having a comparison value that is greater than the threshold value on the display unit with predefined markings;
changing the threshold value in accordance with a user input while the partial images continue to be taken, the threshold value being changed prior to defining an event and prior to determining a point representative of the event;

comparing the comparison values to the changed threshold value after the user input;

defining subregions having a comparison value that is greater than the changed threshold value as events and excluding from evaluation subregions having a comparison value that is lower than the changed threshold value;

determining, for each of the defined events, a point representative of a position of the respective fluorescent dye particle that caused the event; and then generating the complete localization microscopy image of the sample using the partial images based on the points of the defined events.

2. The method as recited in claim 1, wherein prior to defining the events, the subregions whose comparison value is greater than the changed threshold value are marked on the display unit with predefined markings.

3. The method as recited in claim 1, wherein the displaying of the graphical representation of the light distribution, the marking of the subregions and the changing of the threshold value take place during the detecting the fluorescent light.

4. The method as recited in claim 1, wherein the displaying the graphical representation of the light distribution and the marking of the subregions take place after the detecting the fluorescent light.

5. The method as recited in claim 1, wherein a subset of all fluorescent dye particles of the sample is transferred from an inactive state to an active state, and the dye particles in the active state are excited to fluoresce, a number of the dye particles contained in the subset being such that an average distance between the dye particles in the subset is greater than a diffraction resolution limit of the fluorescence microscope.

6. The method as recited in claim 1, wherein a subset of all fluorescent dye particles of the sample is transferred from an active state to an inactive state, and the remaining subset of dye particles in the active state is excited to fluoresce, a number of the dye particles contained in the subset being such that an average distance between the dye particles in the subset is greater than a diffraction resolution limit of the fluorescence microscope.

7. The method as recited in claim 6, wherein the subset of all fluorescent dye particles of the sample is transferred from the active state to the inactive state by subjecting the sample to a bleaching process.

8. The method as recited in claim 1, wherein fluorescent dye particles that automatically change from an inactive state to an active state with a defined probability are included in the sample, and all fluorescent dye particles of the sample are transferred to the inactive state, wherein after a defined period of time selected according to the defined probability, the dye particles in the active state are excited to fluoresce.

9. The method as recited in claim 1, wherein the comparison value is an entire light quantity, light energy, luminous energy, luminance or light intensity within the subregion of the graphical representation of the light distribution with which the comparison value is associated.

10. The method as recited in claim 1, wherein the threshold value is changed during an illumination of the sample over an extended period of time during which the partial images for generating the complete localization microscopy image are taken.

11. The method as recited in claim 10, wherein the threshold value is changed a plurality of times during the illumination of the sample.

12. A device for setting and using a suitable evaluation parameter for stochastic localization microscopy with a fluorescence microscope, the evaluation parameter being useable to prepare for generation of a complete localization microscopy image, the device comprising:

a light source configured to excite a fluorescent dye particles in a sample to fluoresce;

a detector configured to detect fluorescent light originating from the fluorescent dye particles;

a display unit; and an evaluation unit configured to:

prior to generating a complete localization microscopy image:

determine, for a first one of a plurality of partial images taken during the detecting of the fluorescent light, a graphical representation of a distribution of the fluorescent light that is representative of a distribution of a light quantity on the detector of the fluorescence microscope;

generate a signal representative of the graphical representation of light distribution for use in displaying the graphical representation on the display unit;

associate each of a plurality of subregions of the graphical representation of the light distribution with a respective comparison value that is representative of a light quantity in the respective subregion;

use a predefined threshold value as an evaluation parameter during taking of the partial images which are later used to form the complete localization microscopy image;

compare the comparison values to the threshold value;

mark subregions having a comparison value that is greater than the threshold value on the display unit with predefined markings;

change the threshold value after the subregions have been marked in accordance with a user input while the partial images continue to be taken, the threshold value being changed prior to defining an event and prior to determining a point representative of the event;

compare the comparison values to the changed threshold value after the user input;

define subregions having a comparison value that is greater than the changed threshold value as events and exclude from evaluation subregions having a comparison value that is lower than the changed threshold value;

determine, for each of the defined events, a point representative of a position of the respective fluorescent dye particle that caused the event; and then generate the complete localization microscopy image of the sample using the partial images based on the points of the defined events.

* * * * *